(12) United States Patent
Robinson

(10) Patent No.: US 8,387,617 B1
(45) Date of Patent: Mar. 5, 2013

(54) CANISTER DOSAGE INDICATOR DEVICE

(76) Inventor: John H. Robinson, Colorado Springs, CO (US)

( * ) Notice: Subject to any disclaimer, the term of this patent is extended or adjusted under 35 U.S.C. 154(b) by 311 days.

(21) Appl. No.: 12/882,952

(22) Filed: Sep. 15, 2010

(51) Int. Cl.
*A62B 9/00* (2006.01)
*A61M 15/00* (2006.01)

(52) U.S. Cl. ............... 128/205.23; 128/203.12

(58) Field of Classification Search .......... 128/203.12, 128/203.14, 203.15, 203.19, 205.23; 235/87 R, 235/91 R, 103; 222/23, 30, 36–38; 116/279; 137/551, 552, 554, 557
See application file for complete search history.

(56) References Cited

U.S. PATENT DOCUMENTS

| | | | |
|---|---|---|---|
| 3,688,945 A | 9/1972 | Harman, Jr. et al. | |
| 4,662,537 A | 5/1987 | Wolf et al. | |
| 4,984,709 A | 1/1991 | Weinstein | |
| 5,356,012 A | 10/1994 | Tang et al. | |
| 5,544,647 A * | 8/1996 | Jewett et al. | 128/200.23 |
| 5,988,496 A | 11/1999 | Bruna | |
| 6,161,724 A | 12/2000 | Blacker et al. | |
| 6,202,642 B1 * | 3/2001 | McKinnon et al. | 128/200.23 |
| D455,668 S | 4/2002 | Ali-Ahmed | |
| 6,581,797 B2 | 6/2003 | McKinney, Jr. et al. | |
| 2004/0255936 A1 * | 12/2004 | Urbanus | 128/200.23 |
| 2005/0209558 A1 | 9/2005 | Marx | |
| 2006/0081294 A1 * | 4/2006 | Drexel et al. | 137/554 |
| 2007/0084462 A1 * | 4/2007 | Allen et al. | 128/200.23 |
| 2007/0295329 A1 * | 12/2007 | Lieberman et al. | 128/200.23 |

* cited by examiner

*Primary Examiner* — Justine Yu
*Assistant Examiner* — Rachel Young

(57) ABSTRACT

A canister dosage indicator device for counting the number of doses dispensed from a canister. The device features a canister holder having a canister holding portion disposed at the top end and a diaphragm below the canister holding portion. The diaphragm can move between multiple positions including a disengaged position and an engaged position, wherein pressing of a canister in the canister holding portion of compresses the diaphragm to the engaged position. Electrical contacts are disposed on the diaphragm wherein when the diaphragm is in the engaged position the electrical contacts physically contact. A digital counter circuit is connected to the electrical contacts. When the diaphragm moves to the engaged position the count of the digital counter circuit increases by one. A display displays the count of the digital counter circuit.

9 Claims, 3 Drawing Sheets

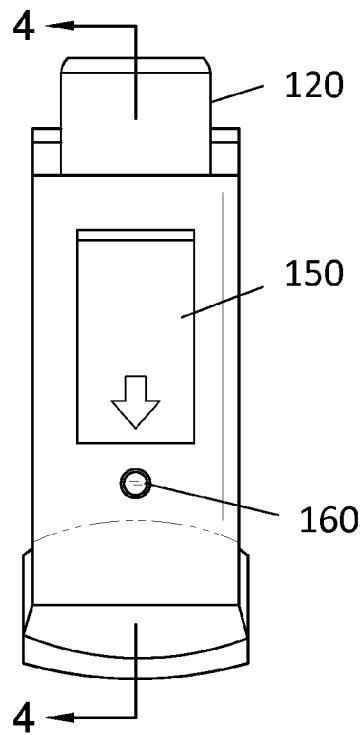
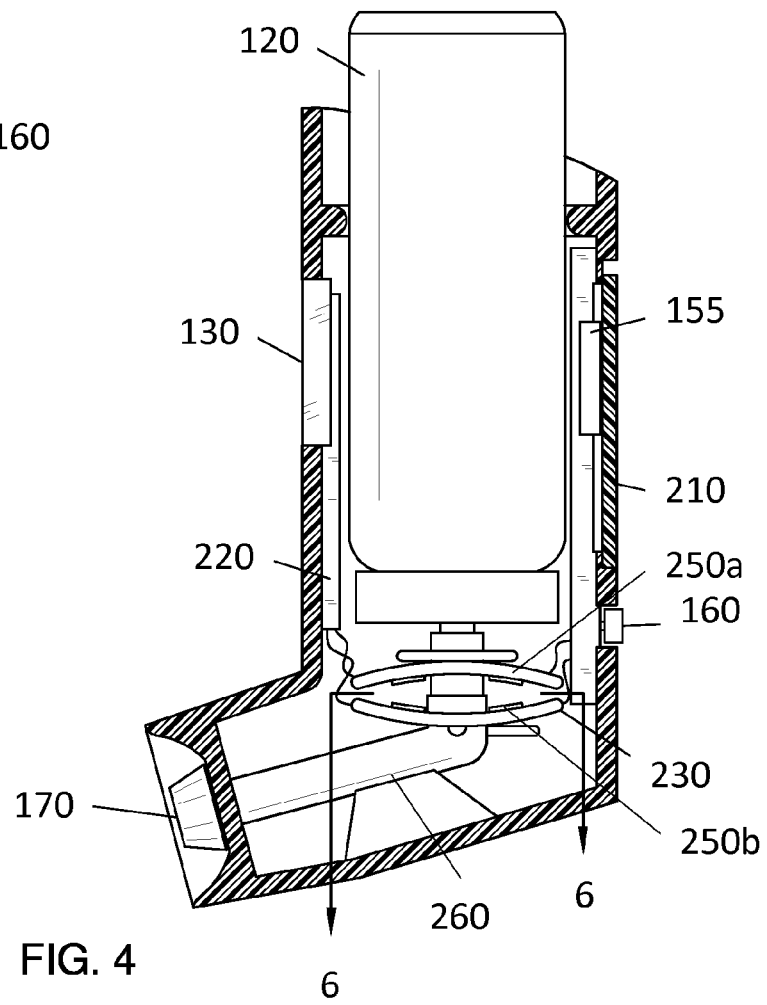

CANISTER DOSAGE INDICATOR DEVICE

FIELD OF THE INVENTION

The present invention is directed to an indicator device for counting the number of doses dispensed from a canister, for example an inhaler canister.

BACKGROUND OF THE INVENTION

Dispensing devices for medication from canisters (e.g., "inhalers") are often used to dispense asthma medications as well as other orally inhaled medications. Oftentimes a user loses track of how many times he/she has dispensed a dose from the canister, leaving the user unsure of when he/she will run out of medication. The present invention features a canister dosage indicator device for counting the number of doses dispensed from a canister. The device of the present invention can help a user keep track of how much medication he/she has used, as well as help prevent a user from purchasing too much medication (e.g., if he/she buys extra medication in fear of running out too soon). More importantly, the device may help to avert a medically dangerous situation where no medication is left in the canister when it is critically needed.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY

The present invention features a canister dosage indicator device. The device may comprise a canister holder having a top end and a bottom end, a canister holding portion is disposed at the top end of the canister holder, the canister holding portion is adapted to receive and hold a canister; a diaphragm disposed in the canister holder below the canister holding portion, the diaphragm comprises an upper half diaphragm situated atop a lower half diaphragm, the diaphragm can move between multiple positions including a disengaged position wherein the upper half diaphragm and lower half diaphragm of the diaphragm are not compressed together and an engaged position wherein the upper half diaphragm and lower half diaphragm of the diaphragm are compressed together, the diaphragm is biased in the disengaged position, wherein pressing of a canister in the canister holding portion of the canister holder compresses the diaphragm to the engaged position; a first set of electrical contacts disposed on the bottom surface of the upper half diaphragm, and a second set of electrical contacts disposed on the top surface of the lower half diaphragm, the first set of electrical contacts are aligned with the second set of electrical contacts such that movement of the diaphragm from the disengaged position to the engaged position causes the first set of electrical contacts and the second set of electrical contacts to physically contact; a digital counter circuit operatively connected to the first set of electrical contacts an the second set of electrical contacts, the digital counter circuit has a count, the count of the digital counter circuit increases by one when the digital counter circuit receives an input signal from the diaphragm when the diaphragm moves to the engaged position and the sets of electrical contacts physically contact; a display disposed on the canister holder, the display is operatively connected to the digital counter circuit, the display is adapted to display the count of the digital counter circuit; a reset button operatively connected to the digital counter circuit, the reset button when activated is adapted to set the count of the digital counter circuit to zero; and a power source operatively connected to either the first set of electrical contacts, the second set of electrical contacts, the digital counter circuit, or the display.

In some embodiments, a mouthpiece is disposed on the bottom end of the shaft of the canister holder. In some embodiments, the mouthpiece further comprises a tube for fluidly connecting to a canister and a valve disposed in the tube near an outer portion of the mouthpiece, the tube and valve together function to help deliver medication from the canister out of the mouthpiece when the canister is pressed. In some embodiments, the digital counter circuit is a microprocessor. In some embodiments, the display is a three segment display. In some embodiments, the display is disposed on an outer surface of the canister holder. In some embodiments, the display may be colored red, green, orange, blue, yellow, or purple. In some embodiments, the power source is a low-voltage battery. In some embodiments, the battery is housed in a battery compartment dispose in the canister holder.

BRIEF DESCRIPTION OF THE DRAWINGS

FIG. 3 is a back view of the canister dosage indicator device of FIG. 1.

FIG. 4 is a side cross sectional view of the canister dosage indicator device of FIG. 3.

DESCRIPTION OF PREFERRED EMBODIMENTS

Figure 1:
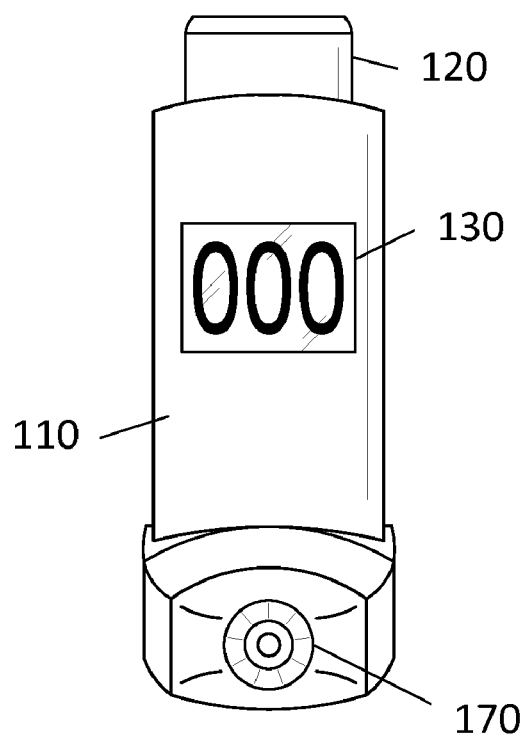
FIG. 1 is a front view of the canister dosage indicator device of the present invention.
Figure 2:
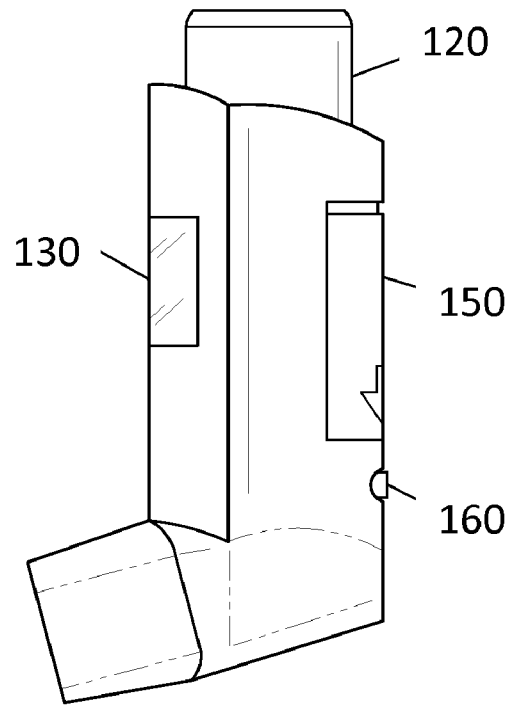
FIG. 2 is a side view of the canister dosage indicator device of FIG. 1.
Figure 5:
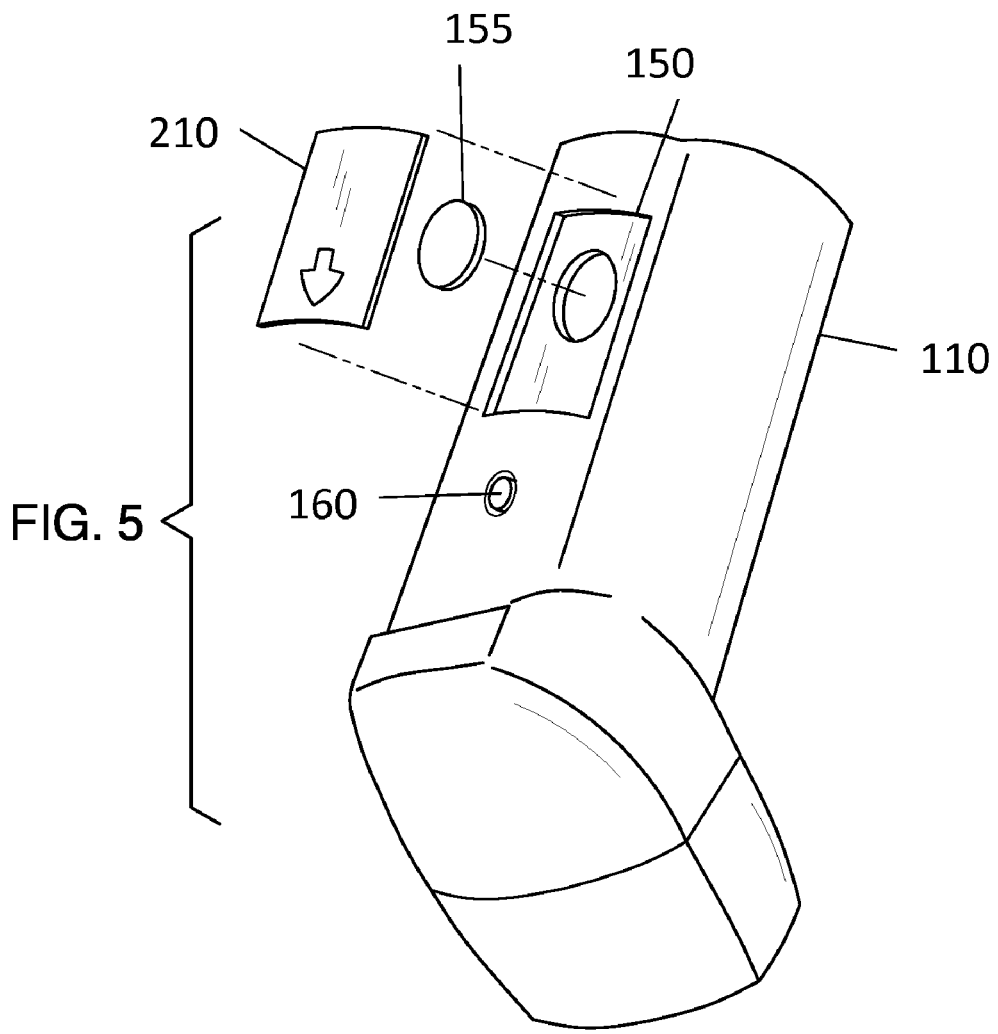
FIG. 5 is a back perspective view of the canister dosage indicator device of FIG. 1.
Figure 6:
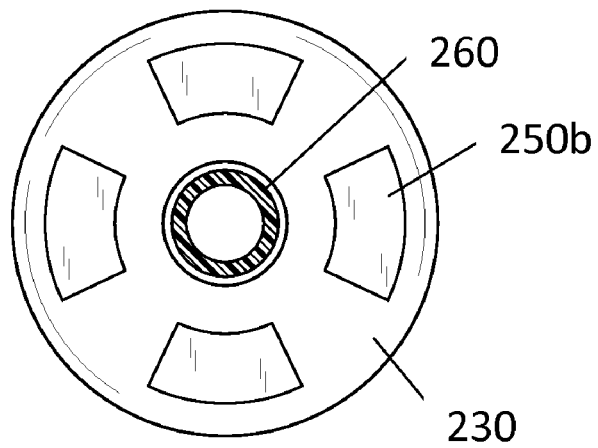
FIG. 6 is a top cross sectional view of the canister dosage indicator device of FIG. 4.

Referring now to FIGS. 1-6, the present invention features a canister dosage indicator device 100 for counting the number of doses dispensed from a canister. The canister dosage indicator device 100 comprises a canister holder/monitoring device (e.g., canister holder 110) for housing a canister 120. Such canisters and canister holders are well known to one of ordinary skill in the art. For example, canister holders are traditionally used for dispensing asthma medication from a canister (e.g., an "inhaler"). For example, the canister holder/monitoring device (e.g., canister holder 110) features an elongated generally hollow shaft adapted to receive and hold the canister 120 and a mouthpiece disposed on the bottom end of the shaft. Generally, the canister 120 is fluidly connected to tube 260 that carries medication released from the canister 120 to a valve 170 at the outer portion of the mouthpiece. To dispense medication from the canister 120, a user generally places the mouthpiece in or near his/her mouth and presses down upon the canister 120. A dose of the medication in the canister 120 is released from the canister 120 and sprayed through the tube 260 and valve 170 into the user's mouth.

Disposed in the canister holder/monitoring device (e.g., canister holder 110) below the canister 120 is a diaphragm 230 comprising an upper half diaphragm situated atop a lower half diaphragm (e.g., the bottom surface of the upper half diaphragm faces the top surface of the lower half diaphragm), where the upper half diaphragm and the lower half diaphragm each have a circular disc shape. The diaphragm 230 can move between multiple positions including a disengaged position wherein the upper half diaphragm and lower half diaphragm of the diaphragm 230 are not compressed together (see FIG. 4) and an engaged position wherein the upper half diaphragm and lower half diaphragm of the diaphragm 230 are compressed together. The diaphragm 230 itself is biased in the disengaged position. Compression of the canister 120 compresses the diaphragm 230 to the engaged position.

A first set of electrical contacts 250a is disposed all around the periphery on the bottom surface of the upper half diaphragm of the diaphragm 230, and a second set of electrical contacts 250b is disposed all around the periphery on the top surface of the bottom half of the diaphragm 230. The first set of electrical contacts 250a are aligned with the second set of electrical contacts 250b such that movement of the diaphragm 230 from the disengaged position to the engaged position causes the first set of electrical contacts 250a and the second set of electrical contacts 250b to physically contact.

The sets of electrical contacts 250 are each operatively connected to a digital counter circuit (e.g., microprocessor 220) disposed in the canister holder/monitoring device (e.g., canister holder 110). The digital counter circuit (e.g., microprocessor 220) is also operatively connected to a display 130 (e.g., three segment display) disposed on the canister holder/monitoring device (e.g., canister holder 110), for example the shaft portion of the canister holder/monitoring device (e.g., canister holder 110).

The digital counter circuit (e.g., microprocessor 220) is adapted to count the number of times the sets of electrical contacts 250 on the diaphragm 230 come into contact, effectively counting the number of doses dispensed from the canister 120. The digital counter circuit (e.g., microprocessor 220) is also adapted to cause the display 130 to display the number of doses counted by the digital counter circuit (e.g., microprocessor 220). For example, if the digital counter circuit (e.g., microprocessor 220) is set at zero (and the display 130 shows "0"), then contact of the electrical contacts 250 via compression of the diaphragm 230 (via compression of the canister 120) causes the digital counter circuit (e.g., microprocessor 220) to add another count, moving the count from zero to one. For example, contact of the electrical contacts 250 sends an input signal to the digital counter circuit (e.g., microprocessor 220) whereupon the digital counter circuit (e.g., microprocessor 220) adds a single count to its previous count. Upon receipt of the input signal, the digital counter circuit (e.g., microprocessor 220) then sends an output command to the display 130 to cause the display 130 to change from "0" to "1." Such digital counter circuits (e.g., microprocessors) are well known to one of ordinary skill in the art.

The device 100 of the present invention further comprises a reset button 160 operatively connected to the digital counter circuit (e.g., microprocessor 220). The reset button 160 is adapted to set the count of the digital counter circuit (e.g., microprocessor 220) to zero. This can be done when loading a new cartridge 120 into the device 100, for example.

The device 100 of the present invention further comprises a power source, for example a low-voltage battery 155. The battery 155 is operatively connected to one or more components of the device 100, for example the electrical contacts 250, the microprocessor 220, the display 130, etc. In some embodiments, the battery 155 is housed in a battery compartment 150 in the canister holder/monitoring device (e.g., canister holder 110), for example see FIG. 5. The battery 155 and battery compartment 150 may be accessible via a door 210 (e.g., for replacement).

The display 130 may be constructed to be illuminated in various colors if desired. For example, in some embodiment, the display 130 may be colored red, green, orange, blue, yellow, purple, or the like. The present invention is not limited to the aforementioned examples.

The disclosures of the following U.S. Patents are incorporated in their entirety by reference herein: U.S. Pat. No. 3,688,945; U.S. Pat. Application No. 2005/0209558; U.S. Pat. No. 4,662,537; U.S. Pat. No. 4,984,709; U.S. Pat. No. 5,356,012; U.S. Design Pat. No. D455,668; U.S. Pat. No. 6,581,797; U.S. Pat. No. 5,988,496; U.S. Pat. No. 6,161,724.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A canister dosage indicator device comprising:
(a) a canister holder having a top end and a bottom end, a canister holding portion is disposed at the top end of the canister holder, the canister holding portion is adapted to receive and hold a canister;
(b) a diaphragm disposed in the canister holder below the canister holding portion, the diaphragm comprises an upper half diaphragm situated atop a lower half diaphragm, the upper half diaphragm and the lower half diaphragm each have a circular disc shape, the diaphragm can move between multiple positions including a disengaged position wherein the upper half diaphragm and lower half diaphragm of the diaphragm are not compressed together and an engaged position wherein the upper half diaphragm and lower half diaphragm of the diaphragm are compressed together, the diaphragm is biased in the disengaged position, wherein pressing of the canister in the canister holding portion of the canister holder compresses the diaphragm to the engaged position;
(c) a first set of electrical contacts disposed all around the periphery on the bottom surface of the upper half diaphragm, and a second set of electrical contacts disposed all around the periphery on the top surface of the lower half diaphragm, the first set of electrical contacts are aligned with the second set of electrical contacts such that movement of the diaphragm from the disengaged position to the engaged position causes the first set of electrical contacts and the second set of electrical contacts to physically contact;
(d) a digital counter circuit operatively connected to the first set of electrical contacts and the second set of electrical contacts, the digital counter circuit has a count, the count of the digital counter circuit increases by one when the digital counter circuit receives an input signal from the diaphragm when the diaphragm moves to the engaged position and the sets of electrical contacts physically contact;
(e) a display disposed on the canister holder, the display is operatively connected to the digital counter circuit, the display is adapted to display the count of the digital counter circuit;

(f) a reset button operatively connected to the digital counter circuit, the reset button when activated is adapted to set the count of the digital counter circuit to zero; and (g) a power source operatively connected to either the first set of electrical contacts, the second set of electrical contacts, the digital counter circuit, or the display.

2. The canister dosage indicator device of claim 1, wherein a mouthpiece is disposed on the bottom end of a shaft of the canister holder.

3. The canister dosage indicator device of claim 2, wherein the mouthpiece further comprises a tube for fluidly connecting to the canister and a valve disposed in the tube near an outer portion of the mouthpiece, the tube and valve together function to help deliver medication from the canister out of the mouthpiece when the canister is pressed.

4. The canister dosage indicator device of claim 1, wherein the digital counter circuit is a microprocessor.

5. The canister dosage indicator device of claim 1, wherein the display is a three segment display.

6. The canister dosage indicator device of claim 1, wherein the display is disposed on an outer surface of the canister holder.

7. The canister dosage indicator device of claim 1, wherein the display may be colored red, green, orange, blue, yellow, or purple.

8. The canister dosage indicator device of claim 1, wherein the power source is a battery.

9. The canister dosage indicator device of claim 1, wherein a battery is housed in a battery compartment disposed in the canister holder.

* * * * *